(12) United States Patent
Takagi et al.

(10) Patent No.: US 8,237,785 B2
(45) Date of Patent: Aug. 7, 2012

(54) AUTOMATIC FOCUSING APPARATUS FOR USE IN A MICROSCOPE IN WHICH FLUORESCENCE EMITTED FROM A CELL IS CAPTURED SO AS TO ACQUIRE A CELL IMAGE, AND AUTOMATIC FOCUSING METHOD THEREFOR

(75) Inventors: Kosuke Takagi, Tokyo (JP); Yuichiro Matsuo, Tokyo (JP); Yoshihiro Shimada, Tokyo (JP)

(73) Assignee: Olympus Corporation, Tokyo (JP)

( * ) Notice: Subject to any disclaimer, the term of this patent is extended or adjusted under 35 U.S.C. 154(b) by 697 days.

(21) Appl. No.: 12/377,257

(22) PCT Filed: Aug. 13, 2007

(86) PCT No.: PCT/JP2007/065820
§ 371 (c)(1),
(2), (4) Date: Feb. 11, 2009

(87) PCT Pub. No.: WO2008/020583
PCT Pub. Date: Feb. 21, 2008

(65) Prior Publication Data
US 2010/0182417 A1    Jul. 22, 2010

(30) Foreign Application Priority Data
Aug. 14, 2006 (JP) ................... 2006-221108

(51) Int. Cl.
*H04N 9/47* (2006.01)
*H04N 7/18* (2006.01)
*H04N 5/243* (2006.01)

(52) U.S. Cl. ............ 348/79; 348/80; 348/254; 348/255; 382/128; 382/133; 435/4; 435/7.23
(58) Field of Classification Search ............ 348/79, 348/80, 254, 255; 382/128, 133; 435/4, 435/7.23
See application file for complete search history.

(56) References Cited

U.S. PATENT DOCUMENTS
5,647,025 A    7/1997    Frost et al.
(Continued)

FOREIGN PATENT DOCUMENTS
JP    02-076480 A    3/1990
(Continued)

OTHER PUBLICATIONS
English Language International Search Report dated Nov. 6, 2007 issued in parent Appln. No. PCT/JP2007/065820, pp. 1-2.

*Primary Examiner* — Haresh N Patel
(74) *Attorney, Agent, or Firm* — Holtz, Holtz, Goodman & Chick, PC

(57) ABSTRACT

In acquisition of an image of cells, a focal position is accurately set at highly active cells rather than focusing on dead cells. Provided is an automatic focusing apparatus (8) used in a microscope (1) that image captures fluorescence emitted from cells to acquire a cell image, the automatic focusing apparatus (8) including a setting unit (5) that sets a luminance range indicating a region where viable cells exist on the basis of a luminance distribution of the acquired cell image; and a focus-detecting unit that detects a focal position on the basis of a luminance of an image of nuclei of the cells within the luminance range set by the setting unit (5).

4 Claims, 6 Drawing Sheets

U.S. PATENT DOCUMENTS

| | | |
|---|---|---|
| 2004/0149882 A1 | 8/2004 | Sasaki et al. |
| 2005/0207639 A1* | 9/2005 | Horiuchi et al. ............ 382/149 |
| 2006/0157637 A1 | 7/2006 | Karasawa et al. |
| 2006/0204236 A1* | 9/2006 | Sasaki et al. ................ 396/265 |

FOREIGN PATENT DOCUMENTS

| | | |
|---|---|---|
| JP | 10-506206 A | 6/1998 |
| JP | 2002-365518 A | 12/2002 |
| JP | 2003-501693 A | 1/2003 |
| JP | 2003-185914 A | 7/2003 |
| JP | 2004-163499 A | 6/2004 |
| JP | 2004-258360 A | 9/2004 |
| JP | 2006-058642 A | 3/2006 |
| JP | 2006-201465 A | 8/2006 |
| WO | WO 00/75709 A1 | 12/2000 |

* cited by examiner

AUTOMATIC FOCUSING APPARATUS FOR USE IN A MICROSCOPE IN WHICH FLUORESCENCE EMITTED FROM A CELL IS CAPTURED SO AS TO ACQUIRE A CELL IMAGE, AND AUTOMATIC FOCUSING METHOD THEREFOR This application is a U.S. National Phase Application under 35 USC 371 of International Application PCT/JP2007/065820 filed Aug. 13, 2007.

TECHNICAL FIELD

The present invention relates to an automatic focusing apparatus, a microscope, and an automatic focusing method for focusing by adjusting the relative distance between, for example, an observed specimen and an objective lens.

BACKGROUND ART

In screening and basic research utilizing cells, there is a known apparatus in the related art for automatically acquiring microscope images of cells (for example, see Patent Document 1).

Automatic focusing of the cell image in Patent Document 1 is performed by using a so-called contrast autofocus process in which the distance between the microscope objective lens and a sample is changed multiple times by an appropriate distance using a motorized alignment mechanism, and the image quality at each position is compared, for example, to select the image with the highest contrast.

As the contrast method in the apparatus described, above a method in which a high-frequency region of the image area is found by using a high-pass filter and the position of maximum contrast in this high-frequency region is set as the focal position is used.

Patent Document 1: Japanese Unexamined Patent Application, Publication No. 2006-58642.

DISCLOSURE OF INVENTION

However, with the apparatus in Patent Document 1, phenomena characteristic of cell images, for example, focus detection errors due to the effect of the luminance of dead cells, are not taken into account.

In other words, a fluorescence image of a cell exhibits different characteristics compared with other images. For example, an image in which the cell nuclei are stained contains cells having an extremely high luminance due to dead cells. In other words, because cells that are dead or dying shrink, their fluorescence is concentrated, and they are generally perceived as having extremely high luminance. One problem with the simple contrast method is that the focal point tends to be set at these high-luminance portions.

On the other hand, information that has biological significance usually contains many high-activity cells (cells that are not dead). Furthermore, in images of cells, there are also many cells where, in particular, the boundary between the nucleus and cytoplasm is not distinct; therefore, the boundary set with a high-pass filter is not necessarily correct and may not correspond to the cell boundary.

Also, when obtaining an image of cultured cells, the cells are often observed to be three-dimensionally superimposed longitudinally.

In such a case, it is preferable to set the focal point at a position where the most numerous cells exist.

The present invention has been conceived in light of the circumstances described above, and it is an object thereof to provide an automatic focusing apparatus, a microscope, and an automatic focusing method which can accurately set a focal position on highly active cells in image acquisition of cells, without focusing on dead cells.

In order to realize the object described above, the present invention provides the following solutions.

A first aspect of the present invention is an automatic focusing apparatus used in a microscope that image captures fluorescence emitted from a cell to acquire a cell image, including a setting unit that sets a luminance range indicating a region where viable cells exist on the basis of a luminance distribution of the acquired cell image; and a focus detection unit for detecting a focal position on the basis of a luminance of an image of nuclei of the cells within the luminance range set by the setting unit.

In the first aspect described above, wherein the setting unit may include an average-luminance calculating unit for calculating an average luminance of the entire cell image and may set a prescribed range on a high-luminance side of the average luminance calculated by the average-luminance calculating unit as the luminance range indicating the existence region in the cell image.

In the first aspect described above, the setting unit may set a minimum point in the luminance distribution on the high luminance side of the luminance of the image of the nuclei as an upper-limit luminance of the region where the viable cells exist.

In the first aspect described above, the setting unit may set a minimum point between the luminance of the image of the nuclei and the average luminance of the entire cell image as a lower-limit luminance of the region where the viable cells exist.

In the first aspect described above, the focus detecting unit may detect a position where a contrast value of the image is maximized as the focal position.

In the first aspect described above, the focus detecting unit may detect the focal position on the basis of a maximum value of the luminances detected at nucleoli inside the nuclei, and the number thereof.

A second aspect of the present invention is a microscope comprising the automatic focusing apparatus described above.

A third aspect of the present invention is an automatic focusing method used during image capturing of fluorescence emitted from a cell, including a step of determining an average luminance of an entire cell image on the basis of a luminance distribution of an acquired cell image; a step of determining a minimum point in the luminance distribution on a high luminance side of a luminance of an image of the nuclei; and a step of detecting a position at which a contrast value of the image is maximized, in a luminance region between the average luminance and the minimum point, as a focal position.

The present invention affords an advantage in that, in image acquisition of cells, it is possible to accurately set the focal position at highly active cells, without focusing on dead cells.

BEST MODE FOR CARRYING OUT THE INVENTION

A focusing apparatus and a microscope 1 equipped therewith according to a first embodiment of the present invention will be described below with reference to FIGS. 1 to 6.

Figure 1:
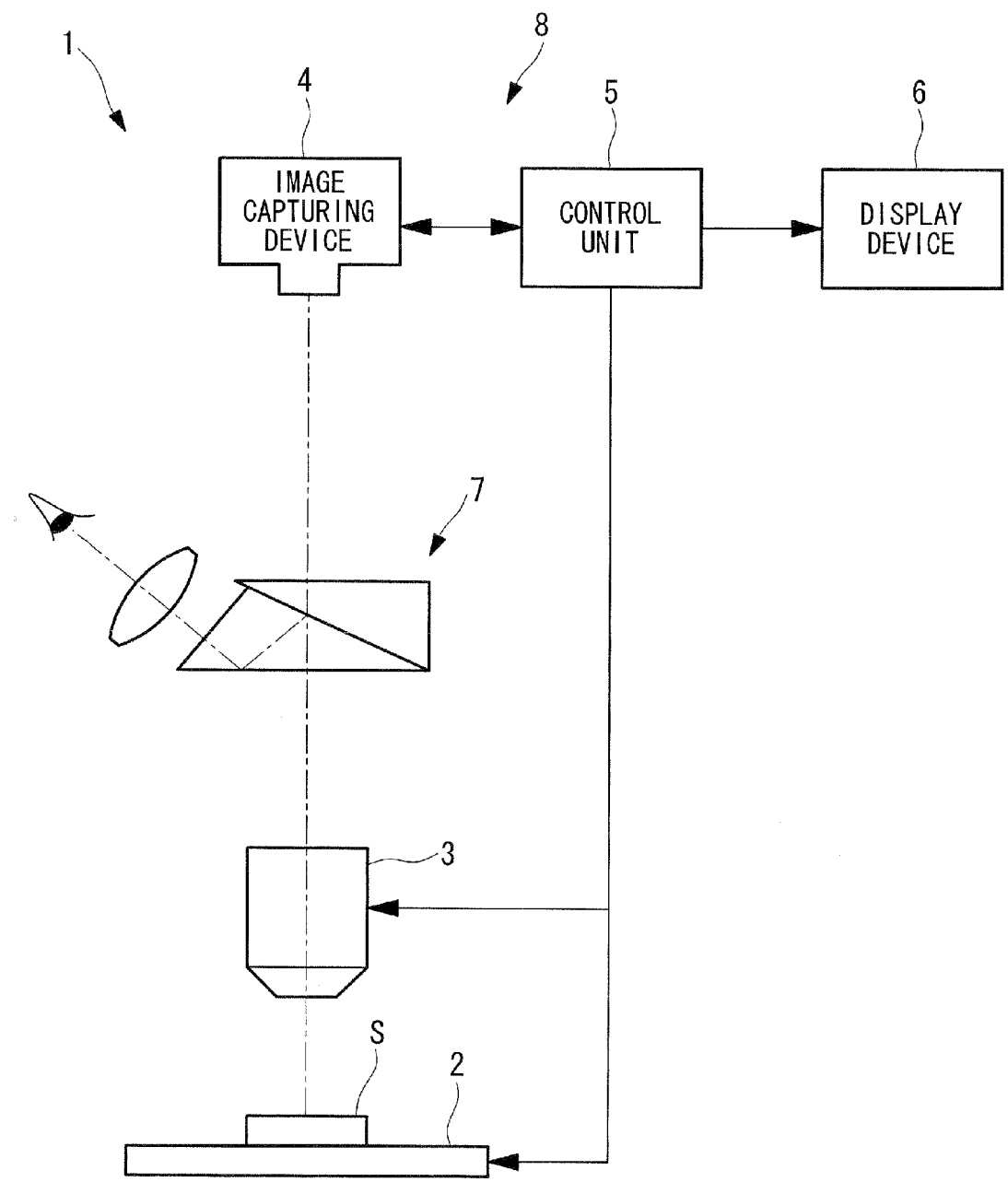
FIG. 1 is an overall schematic structural diagram showing a microscope according to a first embodiment of the present invention.

As shown in FIG. 1, the microscope 1 according to this embodiment includes a stage 2 on which a cell specimen S or the like is mounted and which is moved horizontally in two axial directions; an objective lens 3 that collects fluorescence from the cell specimen S; an image-capturing device 4, such as a CCD camera, that captures an image of the fluorescence collected by the objective lens 3; a control unit 5 that controls these devices; and a display device 6 that displays the image acquired by the image-capturing device 4. Reference symbol 7 in the drawing is an eyepiece optical system for visually observing the cell specimen S directly, with the objective lens 3, or the fluorescence collected from the cell specimen S.

The cell specimen S or the like is arranged to be mounted on a slide glass or multiplate.

An automatic focusing apparatus 8 according to this embodiment is formed of the objective lens 3, which can be adjusted in position in the optical axis direction; the image-capturing device 4, and the control unit 5. In other words, by processing the image of the cell specimen S acquired by the image-capturing device 4 using the control unit 5, an image of the nucleus of a cell (hereinafter referred to as cell nucleus) is specified, and the objective lens 3 is moved so that the focus is coincident with the cell nucleus.

In an image etc. in which the cytoplasm is fluorescence stained, the cells have a variety of shapes; in particular, the shapes of cells in culture conditions are complex because of adhesion of other cells, attachment to the bottom surface of the culture vessel, and so forth.

In contrast, the cell nuclei tend to take a comparatively simple shape such as a circle or ellipse. Because the cell nuclei are comparatively easy to stain, and because many fluorescent substances are available for specifically coloring cell nuclei, they are generally easy to observe.

There is a great deal of biological research directed to the cell nucleus itself, such as the activity of the cell nucleus, the relationship between the cell cycle and cancer, and so on. Furthermore, there are various organelles and mechanisms inside the cell nucleus, and it is comparatively straightforward to identify differences in their levels of fluorescence. Therefore, it is possible to find the most suitable focal position by detecting these and using them in analysis.

Figure 2:
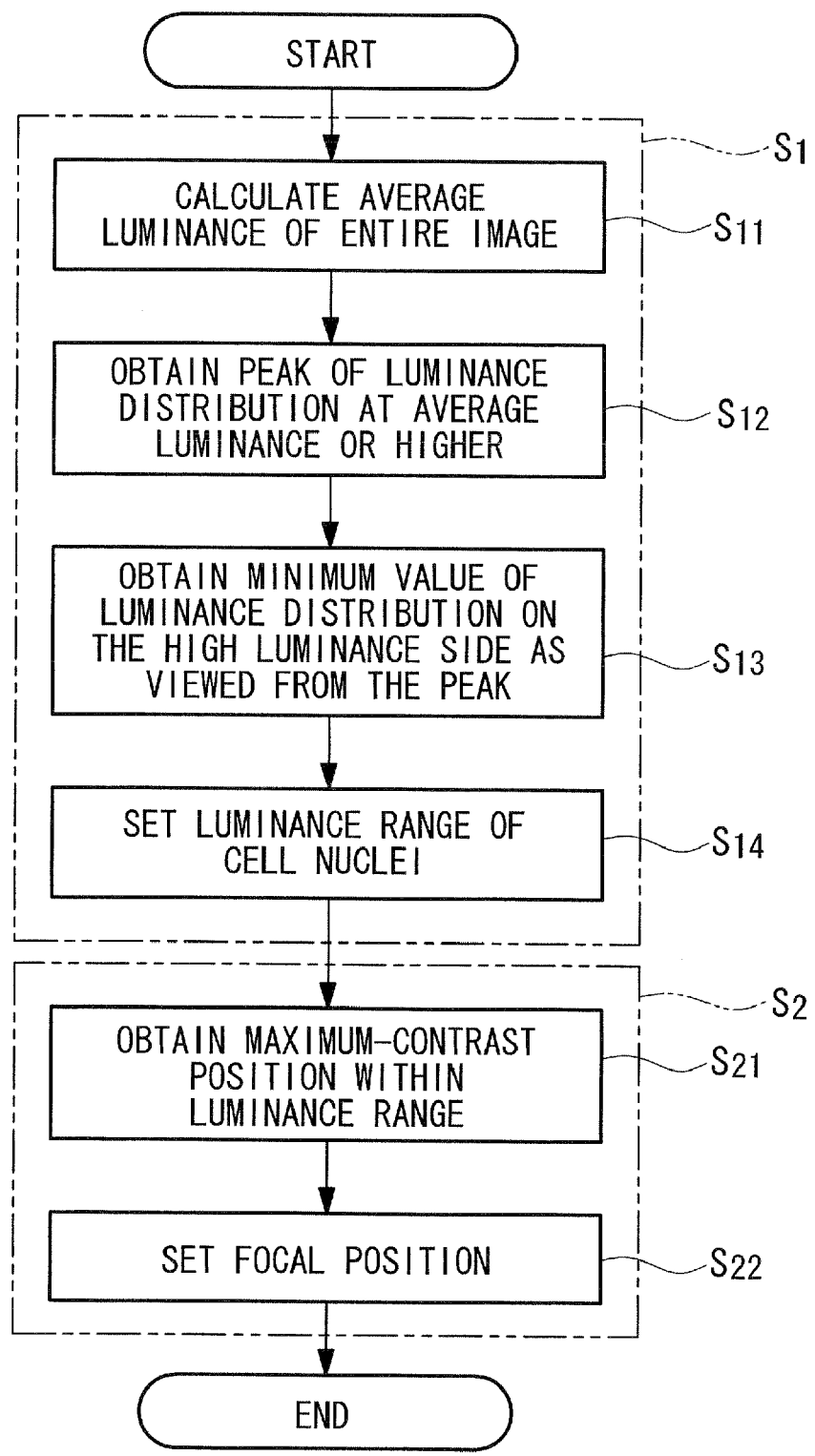
FIG. 2 is a flowchart for explaining an automatic focusing method using the automatic focusing apparatus in the microscope in FIG. 1.

In this embodiment, as shown in FIG. 2, the control unit 5 constituting the automatic focusing apparatus 8 performs a step Si of processing the image of the cell specimen S acquired by the image-capturing device 4 and specifying a luminance range indicating a region where viable cells exist, and a step $S_2$ of detecting the focal position on the basis of the luminance of the image of the cell nuclei inside the specified luminance range.

Specifically, in Step $S_1$, the control unit 5 removes regions of extremely high luminance, such as dead cells P or detritus Q, from an image G of the cell specimen S acquired by the image-capturing device 4 and specifies a luminance range, in a comparatively wide range, indicating the region where viable cells R exist.

Figure 3A:
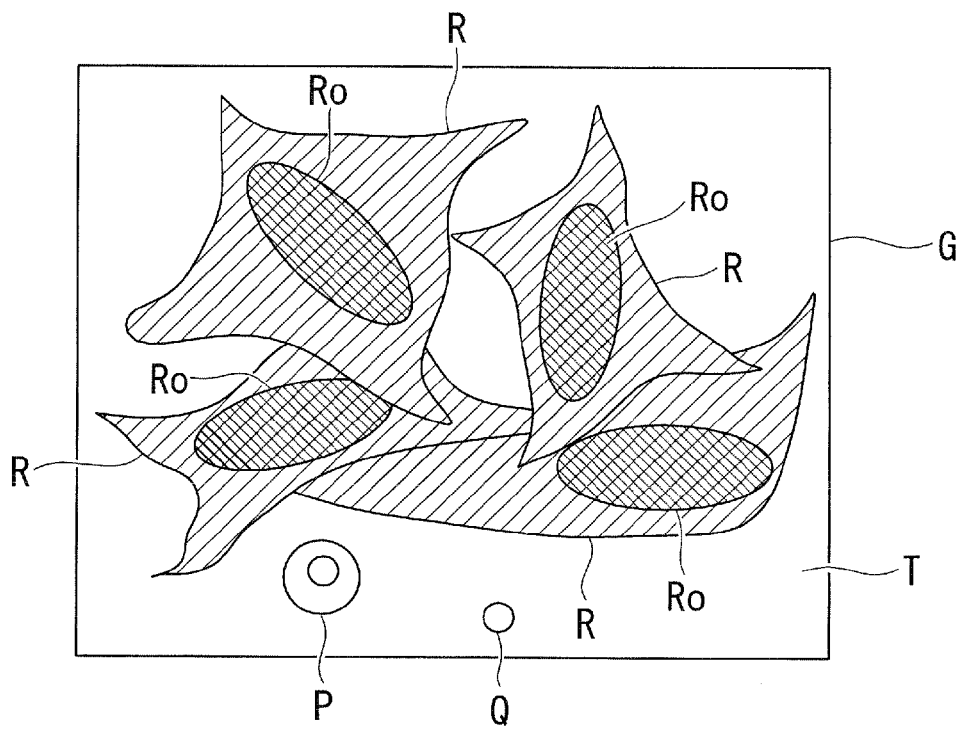
FIG. 3A is a diagram showing an example of an image of a cell specimen, wherein the entire image is shown.
Figure 3B:
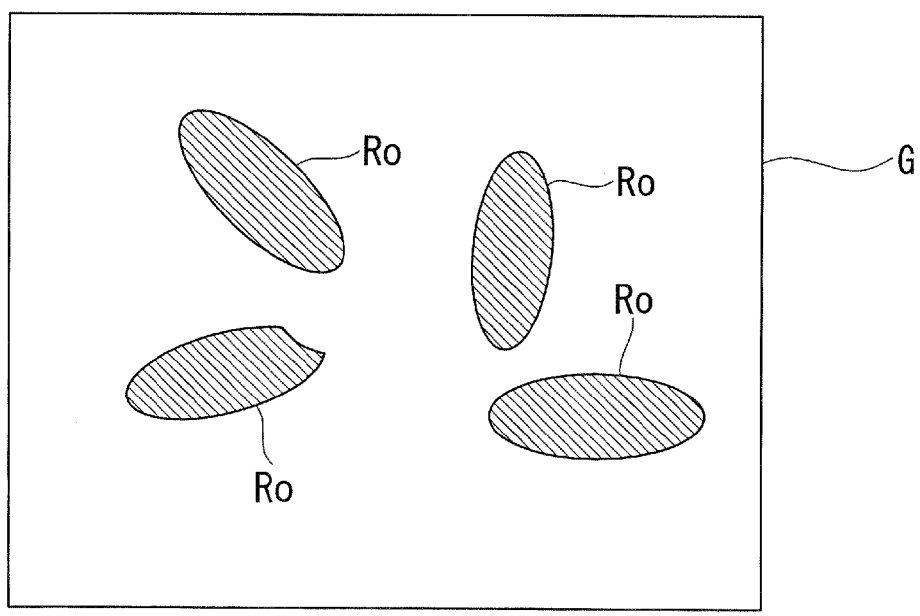
FIG. 3B is a diagram showing an example of an image of a cell specimen, wherein an image of a cell nuclei of viable cells is shown.
Figure 4:
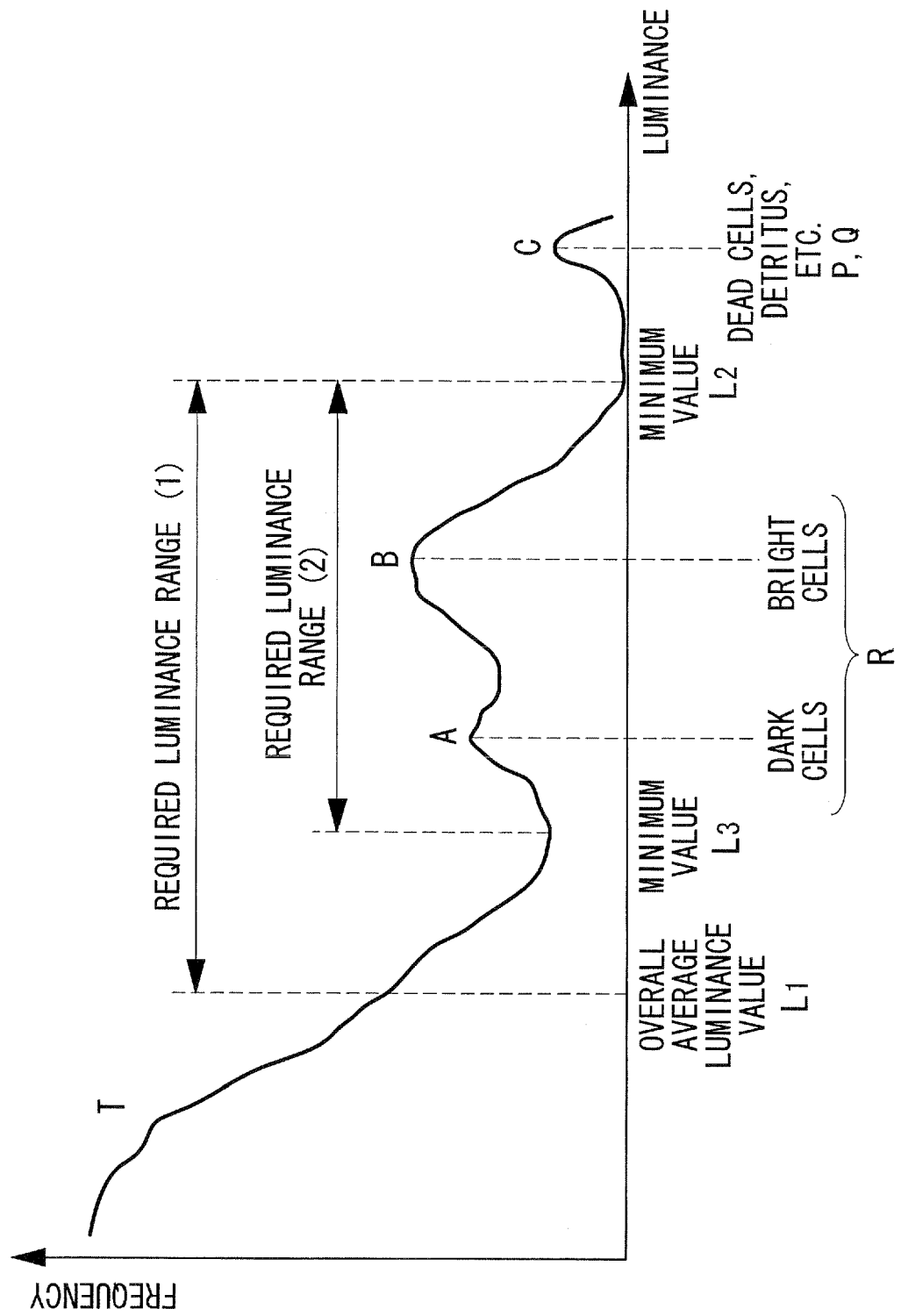
FIG. 4 is a diagram showing a luminance distribution of an entire image of a cell specimen.

As shown in FIGS. 3 to 5, the image of the cell specimen S contains an extremely high-luminance object, such as a dead cell P. Furthermore, the brightness of a cell nucleus $R_0$ is assumed to be related to the amount of chromosomes inside the cell nucleus $R_0$, in other words, to the cell cycle, and the fluorescence level of the cell nucleus $R_0$ takes a wide range of values depending on the activity of the cell.

Cells normally selected for observation are high-activity viable cells R that have not died; however, low-activity viable cells R having a small amount of chromosomes are frequently also selected for observation as a comparison. In other words, to observe the cell nuclei $R_0$ of viable cells R, it is necessary to remove portions with extremely high luminance, such as dead cells P, to identify portions thought to be viable cells R, over a wide range, and to focus on these.

Thus, as shown in FIG. 3B, a luminance value for which the maximum number of viable cells R of interest are predicted to be contained in the image G is determined from the luminance of the image of the cell nuclei $R_0$.

This is described more concretely in the following.

That is, in an actual cell image G, the luminance range corresponding to viable cells R is at a higher position than an average value $L_1$ of the overall luminance. For example, as shown in FIGS. 3A and 3B, in an image G of packed cells, the ratio of cell nuclei $R_0$ is comparatively small, normally about half of the entire image or less.

The image G is generally separated into a background T where no cells exist, viable cells R, dead cells P, and a noise area containing objects other than cells, such as air bubbles or detritus Q.

Furthermore, in the viable cells R, because the image of the cell nucleus $R_0$ occupies a small region at the center of the entire cell, including the cytoplasm, as shown in FIG. 3B, the regions corresponding to the cells in the image of the cell nuclei $R_0$ only occupy about half the area of the entire image G, or less. In other words, looking at the overall image G, because there are a lot of background T regions whose luminance value is substantially zero, as shown in FIG. 4, in the image of the cell nuclei $R_0$, the average luminance of the regions with viable cells R is generally higher than the average luminance value $L_1$ of the entire image.

Figure 5A:
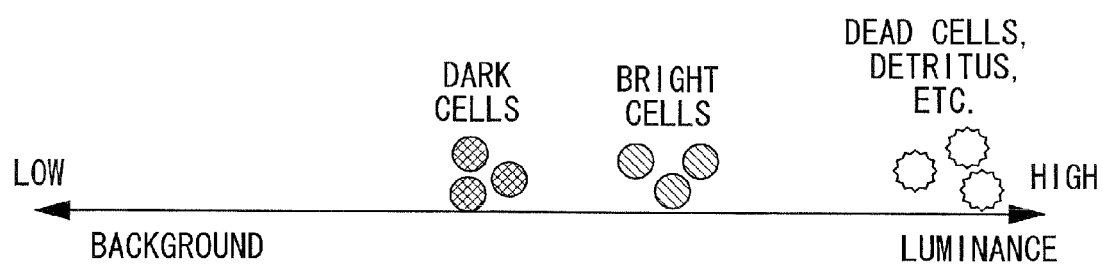
FIG. 5A is a diagram showing a luminance distribution of actual cells having the luminance distribution in FIG. 4.
Figure 5B:
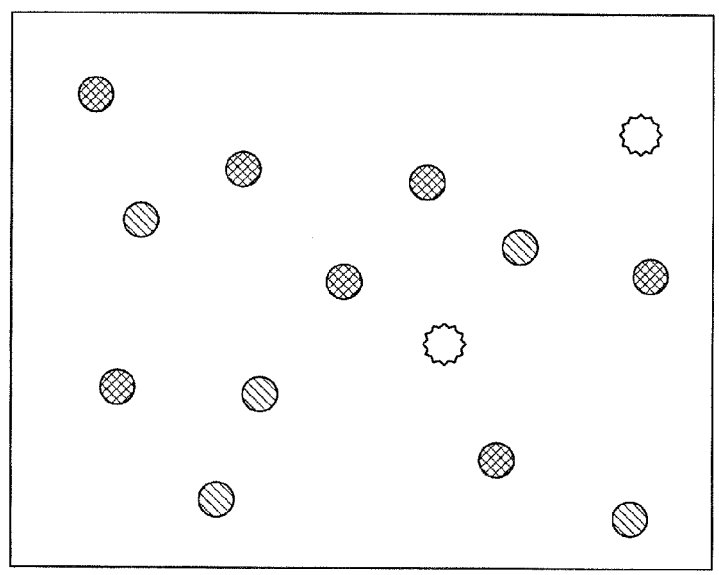
FIG. 5B is a diagram showing an example of a cell image of actual cells having the luminance distribution in FIG. 4.

The luminances of actual cells and their distribution is shown, for example, in FIG. 4, FIG. 5A, and FIG. 5B.

Thus, the control unit 5 first determines the average value $L_1$ of the luminance of the entire cell image G acquired by the image-capturing device 4 (Step S11). The luminance range containing the viable cells R is judged as being either a peak A (luminance of dark cells) or a peak B (luminance of bright cells) in the luminance distribution on the high luminance side of the average luminance value $L_1$ of this entire image G.

Therefore, by selecting the high luminance side of the overall average luminance value $L_1$, it is possible to identify the cell distribution region approximately.

Next, the control unit 5 obtains the peak A or the peak B in the luminance distribution on the high luminance side of the average luminance value $L_1$ of the entire image G (Step S12).

Then, the control unit 5 determines the minimum value $L_2$ in the luminance distribution on the high-luminance side close to the peak A or the peak B described above (Step S13).

As described above, the dead cells P appear as pixels with a luminance higher than the viable cells R, and noise caused by minute detritus Q etc. in the cell image also generally has a high luminance. In addition, the luminance distribution of dead cells P and detritus Q (peak C in FIG. 4) and the luminance distribution of viable cells in the normal cell cycle (peaks A and B in FIG. 4; dark cells and bright cells in FIG. 5A) do not have continuous luminance values; rather, the dead cells P and detritus Q appear on the high-luminance side as the peak C, which is not continuous with the luminance peaks A and B of viable cells R.

Therefore, because the control unit 5 excludes the above-mentioned dead cells P and detritus Q etc., it excludes the discontinuous peak C on the high-luminance side, which is assumed to originate from these. More specifically, for the luminance range required in image capturing, a prescribed range where the above peaks A and B, serving as the luminance distribution of the image of the cell nuclei $R_0$, are defined as a reference, in other words, from the average luminance value $L_1$ of the entire image G to the minimum value $L_2$ described above ("required luminance range (1)" in FIG. 4), is set as the luminance range of viable cells R (Step S14).

On the low-luminance side, an initial minimum value $L_3$ is obtained when going from the average luminance value $L_1$ of the entire image towards the high-luminance side, and the values between this minimum value $L_3$ and the minimum value $L_2$ mentioned above may be set as the luminance range of viable cells R. ("Required luminance range (2)" in FIG. 4.)

In other words, for a luminance distribution containing multiple peaks, the peak luminance values on the high luminance side of the average luminance value $L_1$, and the vicinity thereof, are set as the luminance range of the cell nuclei $R_0$ where the viable cells R exist.

In other words, for the luminance range, the control unit 5 sets the luminance average value $L_1$ of the entire image or the initial minimum value $L_3$ as the lower limit, and the minimum value $L_2$ on the high luminance side of the above-mentioned peak A or peak B as the upper limit. The minimum value $L_2$ on the high luminance side mentioned here is a value for excluding non-continuous high luminances (namely, the peak C on the high-luminance side which is not continuous with the peaks A and B in the luminance distribution), as described above.

By setting this upper limit, noise regions such as dead cells P and detritus Q are eliminated, and by setting the lower limit, the brightness inside the cell nuclei $R_0$ is set as a target luminance of interest.

Next, for each pixel in the luminance range in the cell distribution region determined by the method described above, the control unit 5 calculates the relative position of the objective lens 3 and the cell specimen S where the contrast value in the image G is maximized (Step S21), and sets that position as the focal position (Step S22).

When determining this maximum value, the average value of the luminance/average value of the luminance gradient etc. can be used.

More specifically, for example, the ratio of the average luminance value in the above-described luminance range and the background average luminance value is taken as the average value of the luminance.

Figure 6:
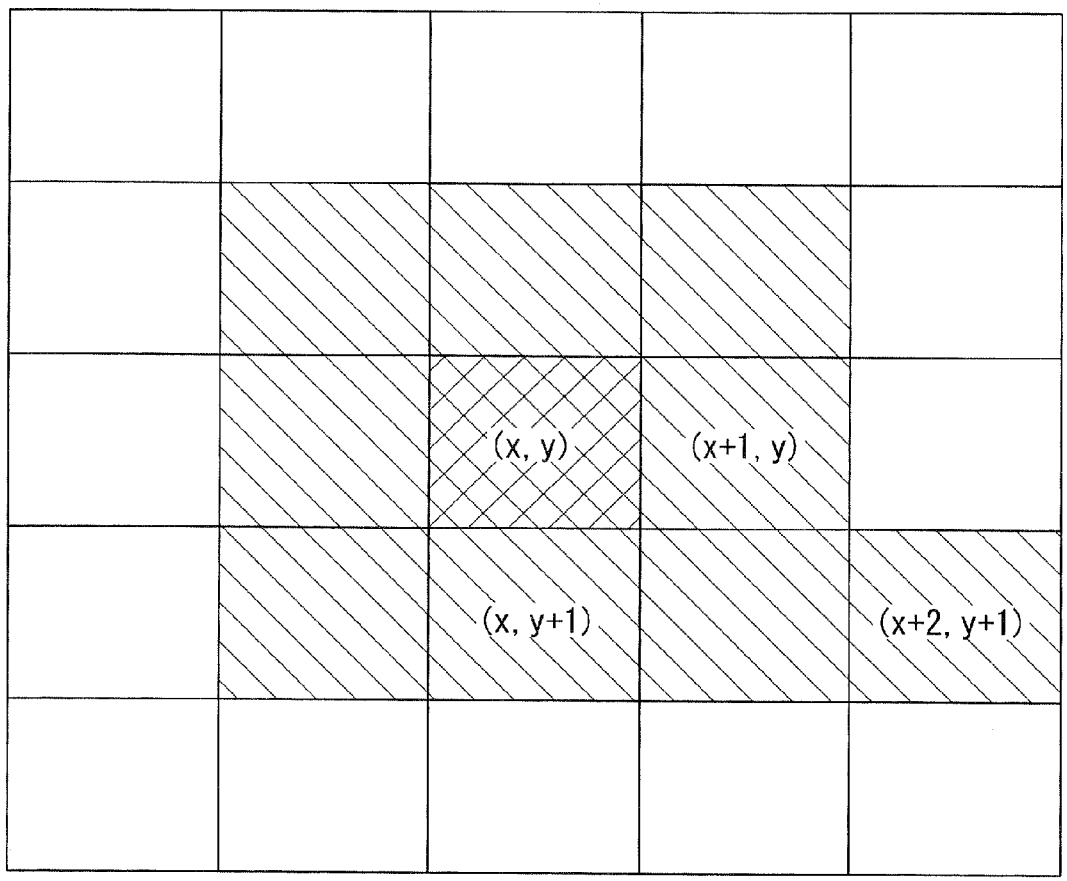
FIG. 6 is a diagram showing an example of a focus-position setting method using the automatic focusing apparatus in the microscope in FIG. 1.

Additionally, as shown in FIG. 6 for example, the differences in luminance between each desired pixel in the luminance range (for example, address (x,y)) and pixels in the vicinity thereof (for example, addresses (x+1, y) and (x, y+1), or address (x+2, y+1) that is not directly neighboring but is separated by a prescribed gap) are used as the luminance gradient. These are used as the contrast value, and the point where this value is maximized is defined as the focal position.

The luminance of interest will be clarified below using an equation, for example.

For example, consider a case in which the position where the average value of the luminance is maximized is set as the focal position. The distribution probability of the luminance in the image at this time is defined as $P(I)$. Here, I is the luminance value. For example, when the number of pixels in an image with a luminance value I=756 is 100 and the number of pixels in the entire image is 1000, the distribution probability $P(756)=0.1$.

Thus, the average value of the luminance is calculated to be $Iav=\Sigma(I \times P(I))$.

Because the weight of each luminance value I contributing to the average value Iav is the distribution probability $P(I)$, to set the focal position at the luminance value I of interest, the distribution probability $P(I)$ should be increased in the region with this luminance value I.

Therefore, by setting the range of luminance values I as described above, it is possible to set the position of the luminance value I of interest as the focal position.

In other words, for large luminance values I, because $I \times P(I)$ is large even if $P(I)$ is small, these must be excluded as far as possible. In particular, when the luminance distribution is discontinuous and the luminance distribution probability $P(I)$ for large luminance values I (here, dead cells P, detritus Q, etc.), as in FIG. 4, $I \times P(I)$ contributing to the average of all dead cells P, detritus Q, etc. is especially large.

Not just the average, but also for values defined with the luminance gradient, luminance differences from neighboring points etc., similarly, when the luminance value I is large, the gradient itself is also large, and therefore, in either case, if there is a discontinuous distribution, such as detritus Q, it is necessary to set the upper limit to exclude it.

Also, because the total number of pixels becomes small by setting the lower limit, it is possible to further enhance $P(I)$, and it is thus possible to increase $I \times P(I)$ in the luminance range of interest.

Moreover, in the image of the cell nuclei $R_0$, it is preferable to set the position where it is possible to better observe the structures inside the cell nuclei $R_0$ as the focal position. These are confirmed using the nucleoli inside the cell nuclei $R_0$.

Specifically, the nucleoli inside the cell nuclei Ro can be detected, for example, as the point where the luminance value in the above-described luminance range is spatially maximized when viewing the image as a two-dimensional plane, and it is possible to set the focal position where optimal observation can be achieved by using the number of nucleoli detected by this method, or the difference in luminance between the nucleoli and nearby points in the vicinity thereof, etc.

Thus, with the automatic focusing apparatus 8, the microscope 1, and the automatic focusing method according to this embodiment, instead of using the entire cell image G in which high-luminance pixels, such as dead cells P and detritus Q, are distributed is not used for determining the focal position, a luminance range indicating the region in which viable cells R exist is set in advance, and the cell image G within that luminance range is used to determine the focal position. Therefore, there is no influence due to the effect of noise, such as dead cells P, and an advantage is afforded in that it is possible to accurately set the focal position at highly active viable cells R.

The invention claimed is:

1. An automatic focusing apparatus for a microscope in which an image of fluorescence emitted from a cell is captured so as to acquire a cell image, the automatic focusing apparatus including a hardware control unit, and the hardware control unit comprising:
   an average-luminance calculating unit for calculating an average luminance of an entirety of the cell image based on a luminance distribution of the acquired cell image;
   a setting unit that sets: (i) as a lower limit luminance of a region where viable cells exist, one of the average luminance calculated by the average-luminance calculating unit and a first minimum point from the average luminance toward a high luminance side in the luminance distribution of the acquired cell image, and (ii) as an upper-limit luminance of the region where the viable cells exist, a second minimum point on the high luminance side of the lower-limit luminance in the luminance distribution of the acquired cell image; and
   a focus detection unit for detecting a position where a contrast value of the image is maximized as a focal position based on a luminance of an image of nuclei of the cells in the acquired cell image within a range between the lower-limit luminance and the upper-limit luminance set by the setting unit.

2. An automatic focusing apparatus according to claim 1, wherein the setting unit sets a minimum point in the luminance distribution on the high luminance side of the luminance of the image of the nuclei as the upper-limit luminance of the region where the viable cells exist.

3. A microscope comprising the automatic focusing apparatus according to claim 1.

4. An automatic focusing method which is performed by a hardware control unit during image capturing of fluorescence emitted from a cell, the automatic focusing method comprising:
   calculating an average luminance of an entirety of an acquired cell image based on a luminance distribution of the acquired cell image;
   setting one of the calculated average luminance and a first minimum point from the average luminance toward a high luminance side in the luminance distribution of the acquired cell image as a lower-limit luminance of a region where viable cells exist;
   setting a second minimum point on the high luminance side of the lower-limit luminance in the luminance distribution of the acquired cell image as an upper-limit luminance of the region where the viable cells exist; and
   detecting a position at which a contrast value of the image is maximized as a focal position based on a luminance of an image of nuclei of the cells in the acquired cell image within a range between the set lower-limit luminance and the set upper-limit luminance.

* * * * *